United States Patent
Chen et al.

(10) Patent No.: US 8,290,230 B2
(45) Date of Patent: Oct. 16, 2012

(54) METHOD AND APPARATUS FOR SUBSTANCE IDENTIFICATION

(75) Inventors: Zhiqiang Chen, Beijing (CN); Li Zhang, Beijing (CN); Kejun Kang, Beijing (CN); Xuewu Wang, Beijing (CN); Qingping Huang, Beijing (CN); Yuanjing Li, Beijing (CN); Yinong Liu, Beijing (CN); Ziran Zhao, Beijing (CN); Yongshun Xiao, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 979 days.

(21) Appl. No.: 12/270,908

(22) Filed: Nov. 14, 2008

(65) Prior Publication Data

US 2009/0129544 A1    May 21, 2009

(30) Foreign Application Priority Data

Nov. 15, 2007    (CN) .......................... 2007 1 0177405

(51) Int. Cl.
   *G06K 9/00*    (2006.01)
(52) U.S. Cl. ............ 382/131; 382/132; 378/51; 378/57; 378/69
(58) Field of Classification Search ................. 382/131, 382/132; 378/57, 51, 69
   See application file for complete search history.

(56) References Cited

U.S. PATENT DOCUMENTS 6,088,423 A * 7/2000 Krug et al. ...................... 378/57

(Continued)

FOREIGN PATENT DOCUMENTS

DE    10 2006 062 009 A1    9/2007

(Continued)

OTHER PUBLICATIONS

Office Action from corresponding Australian Patent Application No. 2008243199, dated May 10, 2010, 2 pgs.

(Continued)

*Primary Examiner* — Tom Y Lu

(74) *Attorney, Agent, or Firm* — Westman, Champlin & Kelly, P.A.

(57) ABSTRACT

A method for substance identification and an apparatus thereof are disclosed. The method comprises comprising steps of: transmitting an object under inspection using high-energy rays and low-energy rays, so as to obtain a high-energy transmission image and a low-energy transmission image for the object, wherein a value of each pixel in the high-energy image indicates a high-energy transparency of the high-energy rays with respect to corresponding parts of the object, and a value of each pixel in the low-energy image indicates a low-energy transparency of the low-energy rays with respect to corresponding parts of the object; calculating a value of a first function for the high-energy transparency and a value of a second function for the high-energy transparency and the low-energy transparency, for each pixel; and classifying locations determined by the value of the first function and the value of the second function using a pre-created classification curve, so as to identify the type of the substance of a part of the object corresponding to each pixel. With the present invention, it is possible to not only obtain a transmission image of the object, but also obtain material information in the object.

24 Claims, 11 Drawing Sheets

U.S. PATENT DOCUMENTS

| | | | |
|---|---|---|---|
| 6,160,866 A | 12/2000 | Mazess et al. | 378/56 |
| 7,092,485 B2 * | 8/2006 | Kravis | 378/57 |
| 7,251,310 B2 * | 7/2007 | Smith | 378/57 |
| 7,369,642 B2 * | 5/2008 | Eilbert et al. | 378/57 |
| 2005/0084069 A1 | 4/2005 | Du et al. | 378/98.9 |
| 2006/0171504 A1 | 8/2006 | Sommer et al. | 378/53 |
| 2007/0025505 A1 | 2/2007 | Bjorkholm | 378/53 |

FOREIGN PATENT DOCUMENTS

| | | |
|---|---|---|
| DE | 10 2007 019 304 A1 | 11/2007 |
| GB | 2 433 777 | 7/2007 |
| GB | 2438278 | 11/2007 |
| JP | 62-161348 | 7/1987 |
| JP | 2287244 | 11/1990 |
| JP | 8068768 | 3/1996 |
| JP | 2005-505216 | 2/2005 |
| JP | 2007-127617 | 5/2007 |
| JP | 2007-183277 | 7/2007 |
| JP | 2007-526482 | 9/2007 |
| JP | 2007-526483 | 9/2007 |
| WO | WO 2005/084352 | 9/2005 |
| WO | 2007/134513 | 11/2007 |

OTHER PUBLICATIONS

"Processing of Interlaced Images in 4-10 MeV Dual Energy Customs System for Material Recognition", by S. Ogorodnikov et al., *The American Physical Society,* 2002, pp. 104701-1-104701-11.

"Approximation Theory" in Wikipedia; Revision Status Jul. 5, 2007, 5 pgs.

Office Action from corresponding German Patent Application No. 10 2008 043 526.0-52, dated Nov. 16, 2009, 4 pgs.

"Combined Search and Examination Report under Section 17 & 18(3)" for Application No. GB0820542.9, United Kingdom Intellectual Property Office, Date of Report Mar. 3, 2009, 4 pages.

Chinese Office Action (with English translation) for Chinese Application No. 2007101774052, dated Jun. 4, 2010, 5 pgs.

Russian Office Action (without English translation) for Russian Application No. 2008144918/28, dated Oct. 12, 2009, 20 pgs.

Japanese Office Action (along with English translation) for Japanese Application No. 2008-292178, dated Jan. 4, 2011, 6 pgs.

\* cited by examiner

FIRST OF CALL, alphaL AND alphaH ARE DEFINED AS FOLLOWS:

$alphaL = (1-\log(TL))*1000$, WHEREIN TL IS THE LOW-ENERGY TRANSPARENCY;

$alphaH = (1-\log(TH))*1000$, WHEREIN TH IS THE HIGH-ENERGY TRANSPARENCY.

THE alphaH IS CONSIDERED AS THE ABSCISSA alphaX OF THE alpha CURVE,
AND THE DIFFERENCE OF alphaL AND alphaH IS CONSIDERED AS THE ORDINATE alphaY OF THE alpha CURVE:

$alphaX = alphaH = (1-\log(TH))*1000$;

$alphaY = alphaL - alphaH = (-\log(TL)+\log(TH))*1000$

Fig. 5

| ORGANIC SUBSTANCE | LIGHT METAL | INORGANIC SUBSTANCE | HEAVY METAL |
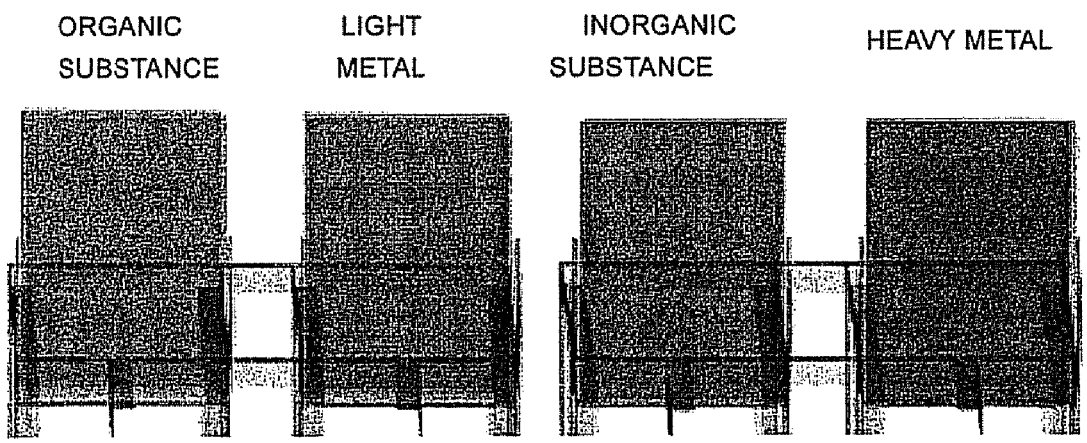
(A)
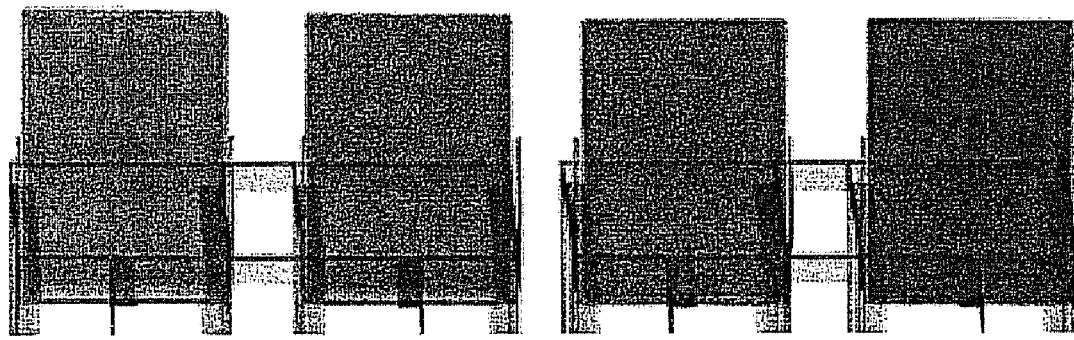
(B)
Fig. 10

METHOD AND APPARATUS FOR SUBSTANCE IDENTIFICATION

The present application claims priority of Chinese patent application Ser. No. 200710177405.2, filed Nov. 15, 2007, the content of which is hereby incorporated by reference in its entirety.

FIELD OF THE INVENTION

The present invention relates to a radiographic technology, more specifically, to a method for substance identification applied in the high-energy X-ray dual-energy imaging inspection system and an apparatus thereof, which are capable of not only acquiring a transmission image of an object under inspection, but also obtaining material information of the object.

BACKGROUND OF THE INVENTION

It is a modern and advanced transportation mode to take a container as a unit for transportation. Containerization has become the main trend of the international cargo transportation. Meanwhile, the uses of containers in smuggling firearms, weapons, drugs, explosives, even WMDs (Weapons of Mass Destruction) and RDDs (Radiological Dispersal Devices) have become an international public hazard troubling every government and interfering with the normal order of the international cargo transportation.

Since 9.11 in U.S., the U.S. government began to attach great importance to the potential risks of the cargo transportation, and worried more about WMDs and RDDs through containers into the United States. To guard against such risks, the U.S. Customs Office issued a "Container Security Initiative (CSI)" in Jan. 17, 2001, in which all the foreign ports with transactions directly linked to the U.S. port were required to be equipped with non-invasive $X(\gamma)$-ray scanning imaging equipments for performing ray-scanning inspections on the containers shipped to the U.S. One year after CSI being announced, there were 18 major ports in the world which joined the initiative and began to operate. In the background where the requirements for the international transportation safety are increasing, the World Customs Organization unanimously adopted a resolution calling for all the 161 members to develop a plan regarding the container security inspection along the mode of the CSI, i.e the container security inspection has become a world's common topic of concern.

The existing container $X(\gamma)$-ray security inspection equipments mainly aim at transmission imaging, i.e. to directly penetrate cargo using X-rays so as to obtain transmission images of all the articles covered by the path of the X-rays. The standard transmission imaging technology solves the "visualization" problem of containers, such that it has been widely used. However, such equipments are usually of the following disadvantages. First, information with a two-dimensional structure is vulnerable to the articles overlapping on the path of the rays. Second, density information is not involved. Third, material information is not involved either.

With respect to a demand for "prevention of smuggling", a main countermeasure against the smuggling is to compare the item information listed in Customs Declaration with high-energy X-ray scanning images of containers, and then inspect whether the above both are matched. Here, the Customs Declaration is priori knowledge, and a standard X-ray transmission imaging technology may substantially meet the above demand. However, the proposal of the CSI makes the demand for the container inspection developing from inspecting of smuggled articles ("prevention of smuggling" for short) to inspecting of dangerous articles ("prevention of danger" for short). Since there are various types of dangerous articles, and they have no fixed shapes, i.e. there is no priori knowledge for articles in the container under inspection, it has already appeared difficult to meet the requirements for the container security inspection only relying on the standard X-ray transmission imaging technology.

The more accurate and efficient security inspection is possible only if more plentiful features of the object is acquired according to the characteristics of WMDs, RDDs and the other dangerous articles. A dual-energy technology uses two kinds of X-ray having different energy spectra to penetrate an object under inspection. Signals acquired under difference energies are processed to obtain the atomic number information of the material for the object. Thus, the security inspection level is efficiently improved to a certain extent by using this technology. It is desirable that the high-energy X-ray imaging container inspection system posses a material discrimination ability, which has become a hot spot of the international research in recent years.

The dual-energy technology is especially efficient when the energy of the X-ray is lower than 200 KeV, which has been widely used in luggage inspection. However, when the energy of the X-ray penetrating the container achieves several MeV, for different materials with the same mass thickness, such as C, Al and Fe, the attenuation over this energy spectrum has no great effect on the attenuation of the ray. Therefore, the material discrimination ability obtained by using the high-energy X-ray imaging is far worse, compared with the low-energy dual-energy X-ray technology. Even some experts in the field of the container inspection believe that the dual-energy imaging technology has almost no effect when the energy of the X-ray is beyond 200 Kev, thus this technology is not suitable for the container inspection system.

SUMMARY OF THE INVENTION

The present invention proposes a substance identification system comprising an energy spectrum shaping means and an automatic calibration means, which may overcome the problem in which material discrimination can not efficiently performed in the high-energy X-ray dual-energy imaging container inspection system in real-time, while visualizing material discrimination information and gray scale information by using an algorithm, such as the dual-energy gray-scale fusion algorithm, the colorization algorithm and the like.

Compared to the traditional high-energy X-ray imaging, using the acquired dual-energy image, the system may not only obtain a fusion image with both of high penetrating power and high contrast sensitivity, but also obtain some material information of cargo, and may have some identification ability for explosives, drugs, radioactive materials and the like, so that the capacity of security inspection for the container may be improved.

In addition, the present invention fully uses advantages of human vision for gray or pseudo color images outputted from the traditional high-energy X-ray imaging system to color images for material discrimination outputted from the high-energy X-ray dual-energy imaging system, so as to provide users with more information.

In an aspect of the present invention, there is provided a method for substance identification, comprising the steps of: transmitting an object under inspection using the high-energy rays and the low-energy rays to obtain a high-energy transmission image and a low-energy transmission image for the object, wherein a value of each pixel in the high-energy image indicates a high-energy transparency of the high-energy rays with respect to corresponding parts of the object, and a value of each pixel in the low-energy image indicates a low-energy transparency of the low-energy rays with respect to corresponding parts of the object; calculating a value of a first function for the high-energy transparency and a value of a second function for the high-energy transparency and the low-energy transparency, for each pixel; and classifying locations determined by the value of the first function and the value of the second function using a pre-created classification curve, so as to identify the type of the substance of a part of the object corresponding to each pixel.

According to an embodiment of the present invention, the method further comprises the steps of setting a neighborhood with a preset size and performing noise reduction on the high-energy image and the low-energy transmission image in the neighborhood of each pixel.

According to an embodiment of the present invention, the step of performing noise reduction on the high-energy image and the low-energy transmission image in the neighborhood of each pixel comprises steps of: searching a pixel similar with the center pixel in the neighborhood, as a similar pixel; and performing weighted averaging on the similar pixel in the neighborhood.

According to an embodiment of the present invention, differences between the high-energy transparency and the low-energy transparency of the similar pixel, and the high-energy transparency and the low-energy transparency of the center pixel, respectively, are both lower than a preset value.

According to an embodiment of the present invention, the object is identified as organic substance, light metals, inorganic substance or heavy metals.

According to an embodiment of the present invention, the method further comprises a step of performing colorization display on an identification result.

According to an embodiment of the present invention, the step of performing colorization display comprises: performing weighted averaging on the high-energy transparency and the low-energy transparency of each pixel, as a fusion gray-scale value; determining a hue according to the type of the material of a part of the object corresponding to the pixel; determining a brightness level of the pixel according to the fusion gray-scale value of the pixel; and obtaining a R value, G value and B value of the pixel from a pre-created look-up table by taking the hue and the brightness level as indices.

According to an embodiment of the present invention, the step of determining a hue according to the type of the material of a part of the object corresponding to the pixel comprises: assigning orange to organic substance, assigning green to light metals, assigning blue to inorganic substance, and assigning purple to heavy metals.

According to an embodiment of the present invention, the method comprises a step of performing spectrum shaping on rays emitted from a ray source, so as to enlarge an energy spectrum difference between the high-energy rays and the low-energy rays.

According to an embodiment of the present invention, the classification curve is created for each type of calibration material through the following steps: obtaining corresponding high-energy transparency and low-energy transparency by irradiating calibration materials with various thicknesses using the high-energy rays and the low-energy rays; forming points of the calibration materials with difference thicknesses by taking the first function of the high-energy transparency as an abscissa and the second function of the low-energy transparency and the high-energy transparency as an ordinate; and forming the classification curve based on the points.

According to an embodiment of the present invention, the step of forming the classification curve based on the points comprises adopting the least square curve fitting method to perform curve fitting on the points.

According to an embodiment of the present invention, the step of forming said classification curve based on the points comprises adopting the optimum fitting polynomial under Chebyshev to perform curve fitting on the points.

According to an embodiment of the present invention, the method further comprises a step of performing discretization on the classification curve.

In another aspect of the present invention, there is provided an apparatus for substance identification comprising: image forming means for transmitting an object under inspection using the high-energy rays and the low-energy rays to obtain a high-energy transmission image and a low-energy transmission image for the object, wherein a value of each pixel in the high-energy image indicates a high-energy transparency of the high-energy rays with respect to corresponding parts of the object, and a value of each pixel in the low-energy image indicates a low-energy transparency of the low-energy rays with respect to corresponding parts of the object; calculating means for calculating a value of a first function for the high-energy transparency and a value of a second function for the high-energy transparency and the low-energy transparency, for each pixel; and classifying means for classifying locations determined by the value of the first function and the value of the second function using a pre-created classification curve, so as to identify the type of the substance of a part of the object corresponding to each pixel.

According to an embodiment of the present invention, the apparatus further comprises means for setting a neighborhood with a preset size and means for performing noise reduction on the high-energy image and the low-energy transmission image in a neighborhood of each pixel.

According to an embodiment of the present invention, the means for performing noise reduction on the high-energy image and the low-energy transmission image in the neighborhood of each pixel comprises means for searching a pixel similar with the center pixel in the neighborhood as a similar pixel and means for performing weighted averaging on the similar pixel in the neighborhood.

The inventive substance identification system is embedded in the high-energy X-ray dual-energy imaging container inspection system, and is adapted to perform shaping on the energy spectrum of the rays by means of designing the spectrum shaping means, thereby improving the material discrimination ability. In addition, through the design for the calibration means, a real-time detection for the system state and an obtainment of a classification parameter which is in best matched with the system state, it is possible to provide a solid foundation for an accurate material discrimination. In addition, through an incorporation of a fast identification algorithm and an image noise reduction algorithm in a material discrimination module, real-time operations of the algorithms are ensured, the effect of the statistical fluctuation of the X-ray data system is drastically reduced, and the accuracy of the material discrimination is ensured.

In addition, the inventive substance identification system may obtain a fusion image with both of the penetrating power and contrast sensitivity by designing a gray-scale fusion algorithm, thus obtaining more information than a single-energy system in terms of gray-scale alone.

After obtaining a result of the material discrimination and a fusion gray-scale image, the present invention further designs a color display module, which may ensure an integrality of the whole data processing procedure from inputting original dual-energy transmission data to outputting RGB color display data.

In addition, the system also gives full consideration to the operation in real-time and performs optimized designs on a variety of algorithms, with a fast operating speed and a good real-time performance.

The present invention may efficiently address the problem in which the high-energy X-ray dual-energy imaging inspection system has a poor material discrimination ability, thus the present invention is of very good material discrimination effects and color display effects, well operability, fast operating speed and high utility value.

BRIEF DESCRIPTION OF THE DRAWINGS

The other objects, features and advantages of the invention will be apparent from the following detailed descriptions of preferred embodiments of the present invention, in combination with the accompanying drawings in which:

FIG. 5 shows a coordinate definition of an alpha curve;

FIG. 10 shows a gray-scale image and a color image.

DETAILED DESCRIPTION OF THE PREFERRED EMBODIMENTS

Hereinafter, the preferred embodiment of the invention will now be described in detail with reference to the accompanying drawings. For clarity, the detailed description of the known function and structure incorporated herein will be omitted, which would otherwise obscure the understanding of the invention.

A substance identification apparatus according to an embodiment of the present invention has a hardware part and a data processing algorithm. The substance identification apparatus is a subsystem embedded in the high-energy X-ray dual-energy imaging container inspection system, which performs material discrimination based on high-energy dual-energy transmission data.

For sake of convenience, rays having high energy level in the high-energy X-rays dual-energy system are referred to as the high-energy level X-rays, rays having low energy level are referred to as the low-energy X-rays. A reasonable selection of an energy spectrum is a premise of the high-energy X-ray dual-energy imaging container inspection system. The selection range of the energy spectrum for the high-energy X-ray dual-energy generally ranges from 3 MeV to 10 MeV. In theory, in an appropriate range of energy, the greater the energy difference is, the better the material discrimination ability is. However, an efficient range for performing material discrimination will become narrow, if the energy difference is too great, and the penetrating power difference between the high-energy level and the low-energy level rays is too great.

Figure 1A:
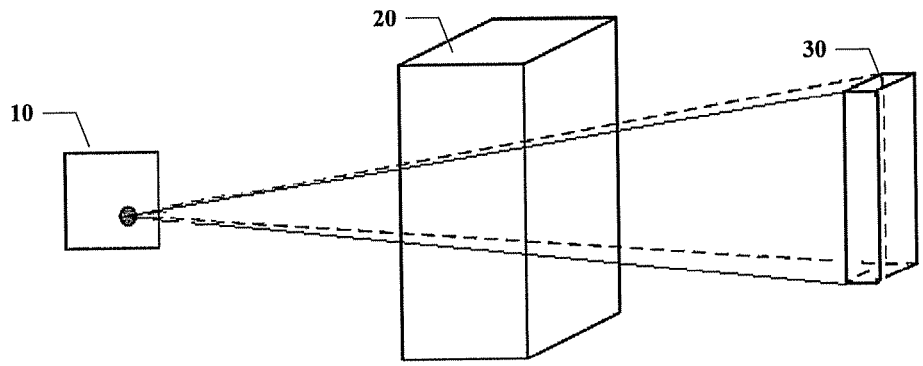
FIG. 1A shows a schematic diagram of basic composition of a high-energy X-ray dual-energy imaging inspection system.
Figure 1B:
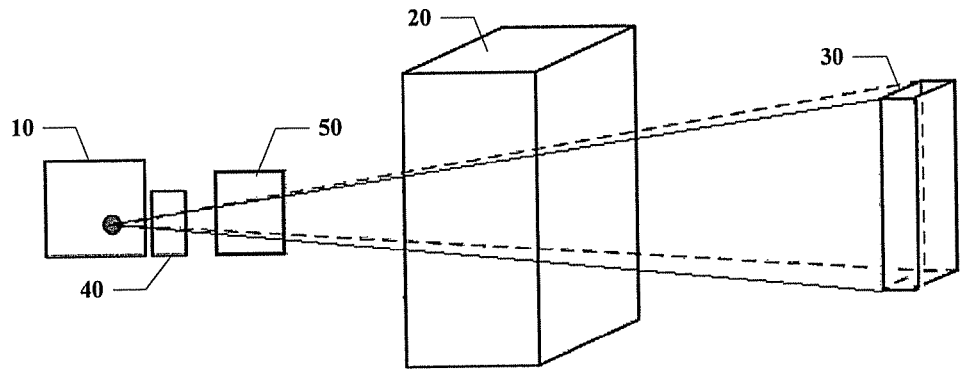
FIG. 1B shows a schematic diagram of a high-energy X-ray dual-energy imaging inspection system embedded with a material identification apparatus.
Figure 1C:
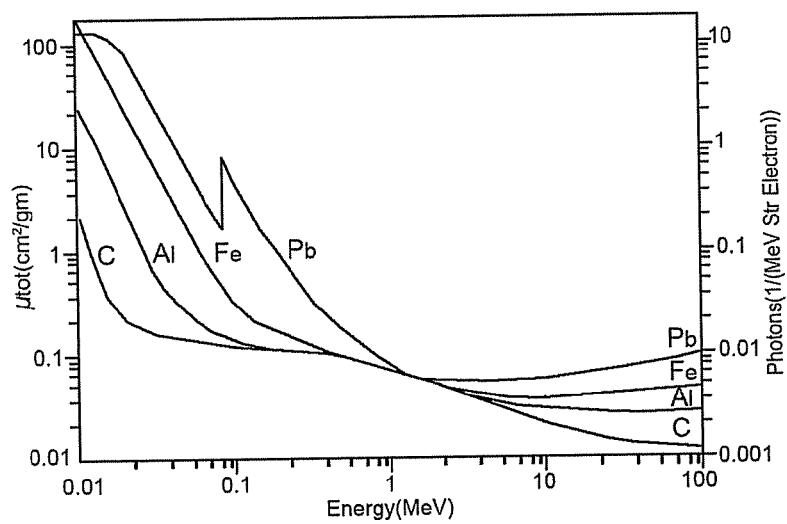
FIG. 1C shows a mass attenuation coefficient curve.

FIGS. 1A and 1B show schematic diagrams of the high-energy X-ray dual-energy imaging container inspection system. As shown in FIG. 1, the high-energy X-ray dual-energy imaging container inspection system has a ray generating device 10, a mechanical driving device (not shown), an object under inspection 20 such as a container, a data acquisition subsystem 30, a scanning control computer and a data processing computer (not shown).

The ray generating device 10 comprises a dual-energy accelerator and the other auxiliary equipments, and may generate X-ray beams with two kinds of energy levels. The mechanical driving device may enable the ray generating device 10 and the data acquisition subsystem 30 to have relative horizontal movements, with respect to the container 20.

It is possible that the ray generating device 10 and the data acquisition subsystem 30 keep still, while the container 20 is in mobile. Alternatively, it is also possible that the container 20 keeps still, while the ray generating device 10 and the data acquisition subsystem 30 are in mobile together.

The data acquisition subsystem 30 mainly comprises linear array detectors, which are used to detect rays obtained after the dual-energy X-ray beams generated by the ray generating device 10 penetrating the object, so as to generate dual-energy transmission data, and are used to transfer the data to the computer (not shown). The data acquisition subsystem 30 further comprises a readout circuit for reading out projection data and a logic circuit control unit on the detector, and the like. The detector may be a solid detector, a gas detector or a semiconductor detector.

The scanning control computer is responsible for inspecting the main control including mechanical control, electrical control and security chain control of the system operation process. The data processing computer is responsible for processing and displaying the dual-energy transmission data obtained by the data acquisition subsystem.

An energy spectrum shaping device 40 and an automatic calibration device 50 as shown in FIG. 1B are introduced to improve the material discrimination ability of the dual-energy system, thereby improving the effect of substance identification.

The energy spectrum shaping device 40 comprises energy spectrum shaping materials and corresponding auxiliary devices. The energy spectrum shaping device 40 is arranged between the ray generating device 10 and the object 20, with a purpose for shaping energy spectra of the rays outputted from the ray generating device 10, prior to the rays penetrating the object 20, so that the energy spectrum distribution is more favorable for the material discrimination.

The characteristic of the energy spectrum shaping material consist in having a very large attenuation for rays with low-energy, and a very small attenuation for rays with high-energy. The better this characteristic is, the better the effect of the energy spectrum shaping is. A material may be considered as an energy spectrum shaping material, once it fulfills the above characteristic. Depending on the characteristic of the energy spectrum shaping material, the equivalent energy of the rays may be improved after the energy spectrum shaping. If the energy spectrum shaping material acts on the rays having high-energy level, the equivalent energy of the rays having high-energy level will be improved, while the equivalent energy of the rays having low-energy level keeps constant, thereby enlarging the energy difference between the high energy rays and the low energy rays, so that the material discrimination ability of the system will be improved.

Figure 2:
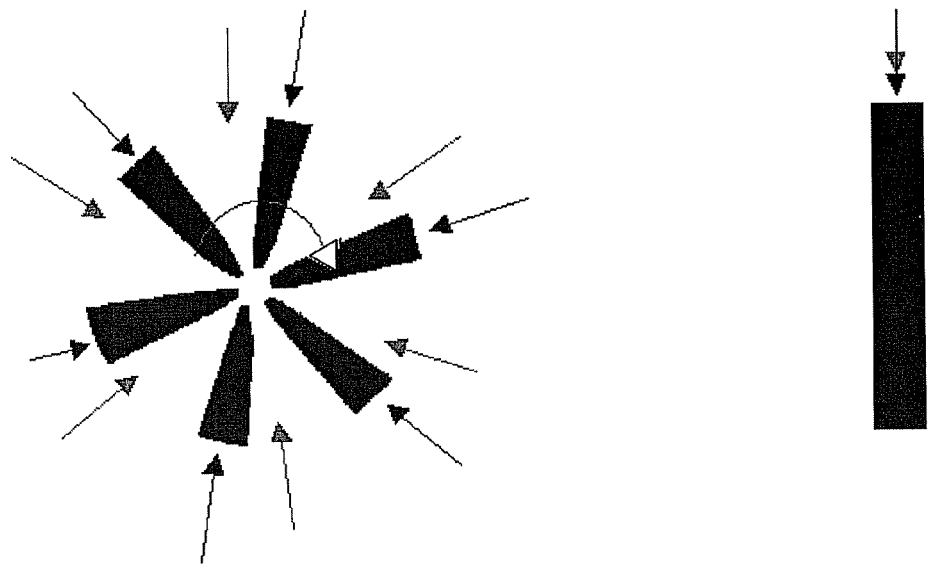
FIG. 2 is a schematic diagram of an energy spectrum shaping means according to an embodiment of the present invention, in which black arrows denote the rays having high-energy level, gray arrows denote the rays having low-energy level, and a black region denotes a shaping material block.

Based on this characteristic, graphite may be selected as a shaping material. From a pure theoretical view, the thicker the shaping material is, the better the material discrimination ability is. However, the thicker the shaping material is, the greater the attenuation degree of the rays is, the lower amount that the detector receives is, and the lower the signal to noise ratio of the data is, when taking the statistical fluctuations into account. As a result, the thickness of the shaping material has an optimum value which needs to be determined based on the actual situation of the system. According to the energy distributions of the high-energy level and low-energy level rays, it is determined that the energy spectrum shaping may be performed only over a certain energy level. FIG. 2A shows a schematic diagram of a rotary-type energy spectrum shaping device. Alternatively, it is possible to perform energy spectrum shaping on both of the high energy level and the low energy level. FIG. 2B shows an energy spectrum shaping device for performing energy spectrum shaping on the both energy levels.

The design of the energy spectrum shaping device 40 should depend on the requirements for the energy spectrum shaping. It is possible to perform shaping only on the high-energy level rays, and then to enlarge the energy difference between the both energy levels by improving the equivalent energy of the high-energy level rays so as to improve the material discrimination ability of the system. It is also possible to perform energy spectrum shaping on the both energy levels, which is a bit special, usually applied in the case when the low-energy level rays stay around 3 MeV. It can be seen from the mass attenuation coefficient curve in FIG. 1C that the attenuation coefficients of low-Z material are close with each other in the vicinity of 3 MeV energy band, and that the change trend is very slow. As a result, the energy change has a very small effect on the discrimination ability of low-Z materials in the vicinity of this energy band, while the attenuation coefficients of high-Z materials have an inflection point in the vicinity of 3 MeV. This will result in that lead(Pb) can not be distinguished from the other materials under such an energy selection. Therefore, the energy spectrum shaping may also be performed on the low-energy level energy of 3 MeV. It is possible to improve the distinguishability of the high-Z materials by using the energy spectrum shaping materials to absorb the low-energy portion of the low-energy level energy, and there is no negative effect on the low-Z materials.

Figure 3:
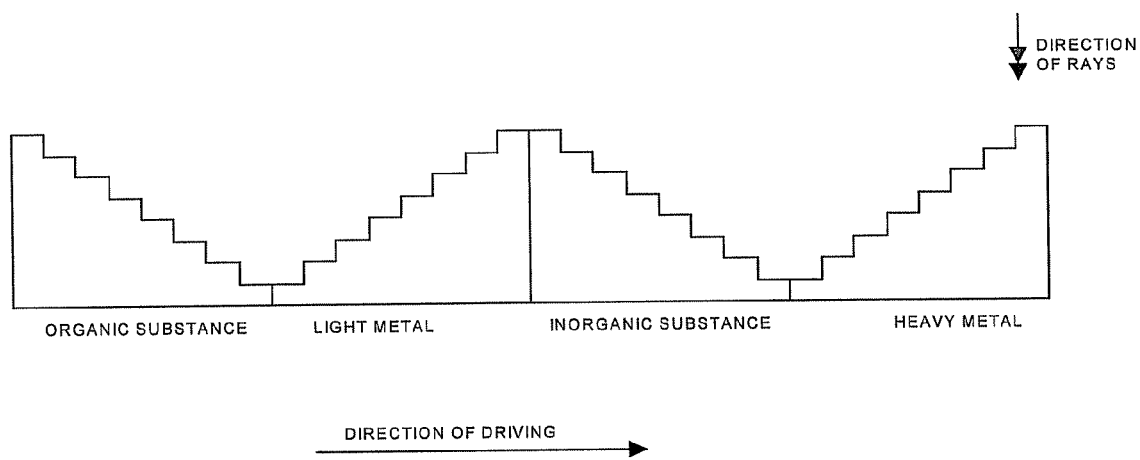
FIG. 3 is a schematic diagram of an automatic calibration means according to an embodiment of the present invention, in which black arrows denote the rays having high-energy level, and gray arrows denote the rays having low-energy level.

FIG. 3 is a schematic diagram of an automatic calibration device according to an embodiment of the present invention. The automatic calibration device has two major parts, i.e. hardware and software.

The automatic calibration device 50 comprises calibration materials which are distributed in ladder and corresponding auxiliary equipments. The automatic calibration device 50 can acquires calibration data, enters the automatic calibration process, obtains a classification parameter matched with the system state in real-time, and saves it in a file as an input to a material discrimination module.

Here, the calibration materials comprise various typical materials. To ensure calibration accuracy, at least one type of typical material may be prepared per category. Alternatively, several types of typical materials with difference equivalent atomic numbers may be prepared per category. If there is no material prepared, or there is a limited space for placing the automatic calibration device 50, the materials of middle categories may be omitted, and the automatic calibration algorithm may use an interpolated value of data of the adjacent category instead. The selection of the calibration materials may be associated with the material discrimination requirements for the system. The requirements for the high-energy X-ray dual-energy may be divided into four categories, i.e. organic substance, light metals, inorganic substance and heavy metals. Therefore, four types of typical materials are selected from the above four categories, i.e. graphite (Z=6), aluminum (Z=13), iron (Z=26) and lead (Z=82) in turn. The selection of these four types of materials is based on two reasons. One is these materials are commonly used, and the other is each of them belongs to an elementary substance, which is of stable nature.

For each material, several classes of ladders should be designed from thin to thick. The thinnest thickness and the thickest thickness depend on the material discrimination range of the system. The number of the classes of the ladders may be decided by the calibration accuracy in together with the space for placing the automatic calibration device.

The auxiliary devices mainly provide the mechanical driving and realize the localization scanning so as to obtain dual-energy transmission data of each ladder for each material. When several columns of dual-energy transmission data are required at each localization point, more than 256 columns are recommended to scan, thereby largely eliminating the effect of the signal statistical fluctuation.

In the direction of the height, the angular distributions for the X-rays, received by the different detectors, over the arm supports of the detectors are different. The spectrum distributions for different angular distributions are different, thereby leading to different parameters for the material discrimination. Therefore, taking the effect of the angular distributions of the X-rays into account, all of the detecting heights may be divided into several regions, each having an independent statistic, so as to generate a classification parameter. This requires that the calibration materials in the automatic calibration device 50 should cover all the spans of interest.

If the heights of the calibration materials are limited by objective factors, such as the processing capacity, the equipment space, and so on. It is impossible to cover all the detector modules on the art support. A simplified manner is as follows. Under normal circumstances, the most interested detecting height is located in a position where the container places cargo, and the system usually adjusts the main beam of the X-ray to the vicinity of that position. As a result, the main beam of the rays is focused on the important calibration object. The calibration materials may be designed to only cover the region. Then the obtained dual-energy transmission data is inputted into the automatic calibration algorithm as its parameter, to generate a classification parameter corresponding to the energy spectrum distribution in the main beam direction of the X-ray, as a classification parameter for all of the detecting regions. This simplified manner lies within the allowance error range, with the angular distribution of the X-ray being smaller.

The calibration materials in the automatic calibration device 50 may be designed to be in any forms as long as the above requirements are met. In FIG. 3, the order number of the ladder and the thickness are described only for illustration, without indicating any actual meanings.

Figure 4A:
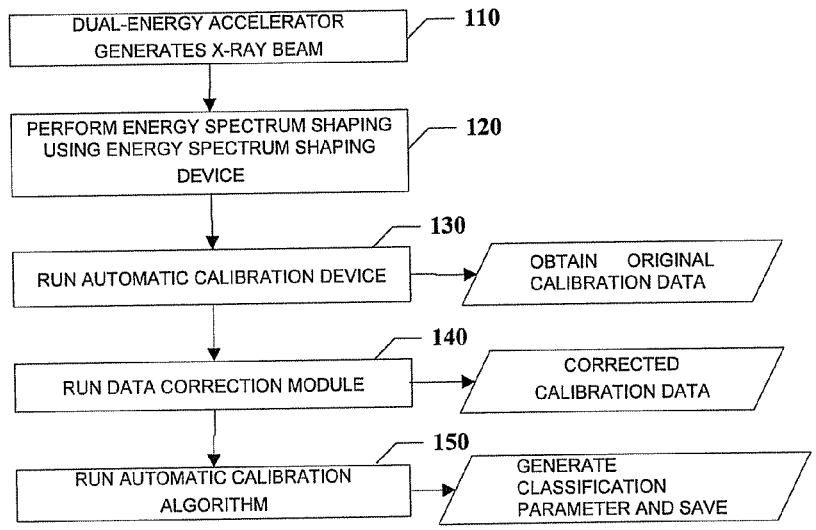
FIG. 4A shows a flowchart of illustrating an automatic calibration process according to an embodiment of the present invention.

FIG. 4A shows a flowchart of an automatic calibration process according to an embodiment of the present invention. As shown in FIG. 4A, the ray generating device 10 generates an X-ray beam at block 110. At block 120, the X-ray beam is shaped by the energy spectrum shaping device 40. At block 130, the automatic calibration process is enabled artificially and run, when the automatic calibration processing is to be performed, so as to obtain original calibration data.

Sequentially, a data correction processing is performed on the original calibration data at block 140. At block 150, an automatic calibration algorithm is run to generate a classification parameter, for being saved in a file.

Then, at block 150, the automatic calibration algorithm is called to calculate the classification parameter matching with the current system state.

Figure 4B:
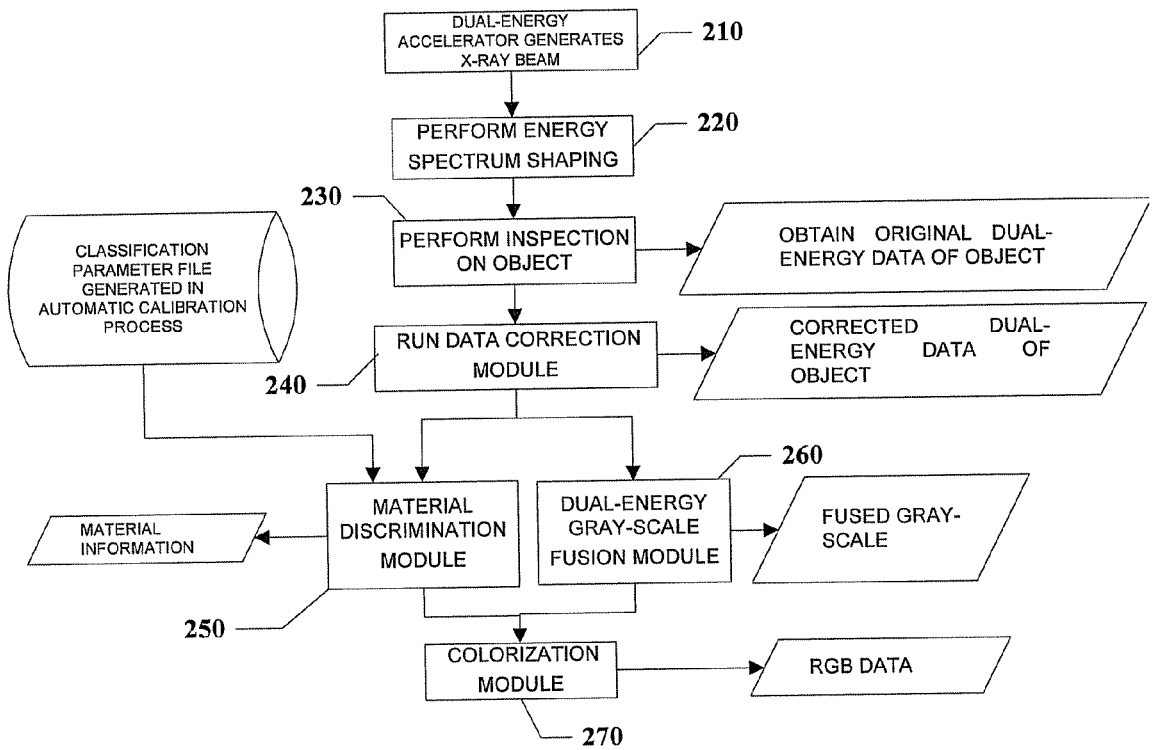
FIG. 4B shows a flowchart of illustrating a substance identification method according to an embodiment of the present invention.

FIG. 4B shows a flowchart of a substance identification method according to an embodiment of the present invention. As shown in FIG. 4B, the ray generating device 10 generates an X-ray beam at block 210, then at block 220, the energy spectrum shaping device 40 shapes the X-ray beam so as to obtain an X-ray beam which is desirable for material discrimination.

At block 230, the shaped X-ray beam penetrates the object 20 to generate original dual-energy data for the object. Thereafter, at block 240, a data correction module is enabled to perform a data correction on the original dual-energy data so as to eliminate effects of background data of the detector, inconsistencies of the detector, and fluctuations of amount of rays. The corrected data is used for the material discrimination and the dual-energy gray-scale fusion processing.

Thereafter, at block 250, a classification parameter file generated during the automatic calibration process is inputted into the material discrimination module. Then the material of the object is identified based on the corrected dual-energy data to generate material information.

On the other hand, at block 260, the corrected dual-energy data is inputted into a dual-energy gray-scale fusion module for a gray-scale fusion processing so as to generate a transmission image for the object with the fused dual-energy data. At this point, at block 280, a colorization processing is performed on the material information outputted by the material classification module. That is to say, a transmission image data suitable for the gray-scale display is converted into RGB data suitable for the color display according to the material information contained in the object, for being displayed on the data processing computer, at block 290.

As described above, once the system state is changed, the automatic calibration process is triggered artificially to enable the automatic calibration device 50 to acquire the spectrum-shaped original calibration data and then to send the data to the data processing computer by the data acquisition subsystem. A material discrimination algorithm is designed using an alpha curve method. Therefore, the purpose of the automatic calibration algorithm is to calculate a classification parameter matching with the system state for the alpha curve diagram. Through calling the automatic calibration algorithm, the classification parameter matching with the system state for the alpha curve diagram is obtained and saved in a file as a parameter input to the material discrimination module. The coordinate of the alpha curve diagram is defined as FIG. 5.

As shown in FIG. 5, alphaL and alphaH are defined as follows.

$$alphaL=(1-\log(TL))*1000, \text{ wherein } TL \text{ is the low-energy transparency;}$$

$$alphaH=(1-\log(TH))*1000, \text{ wherein } TH \text{ is the high-energy transparency.}$$

The alphaH is considered as the abscissa alphax of the alpha curve, and the difference of alphaL and alphaH is considered as the ordinate alphay of the alpha curve:

$$alphax=alphaH=(1-\log(TH))*1000;$$

$$alphay=alphaL-alphaH=(-\log(TL)+\log(TH))*1000.$$

Figure 6A:
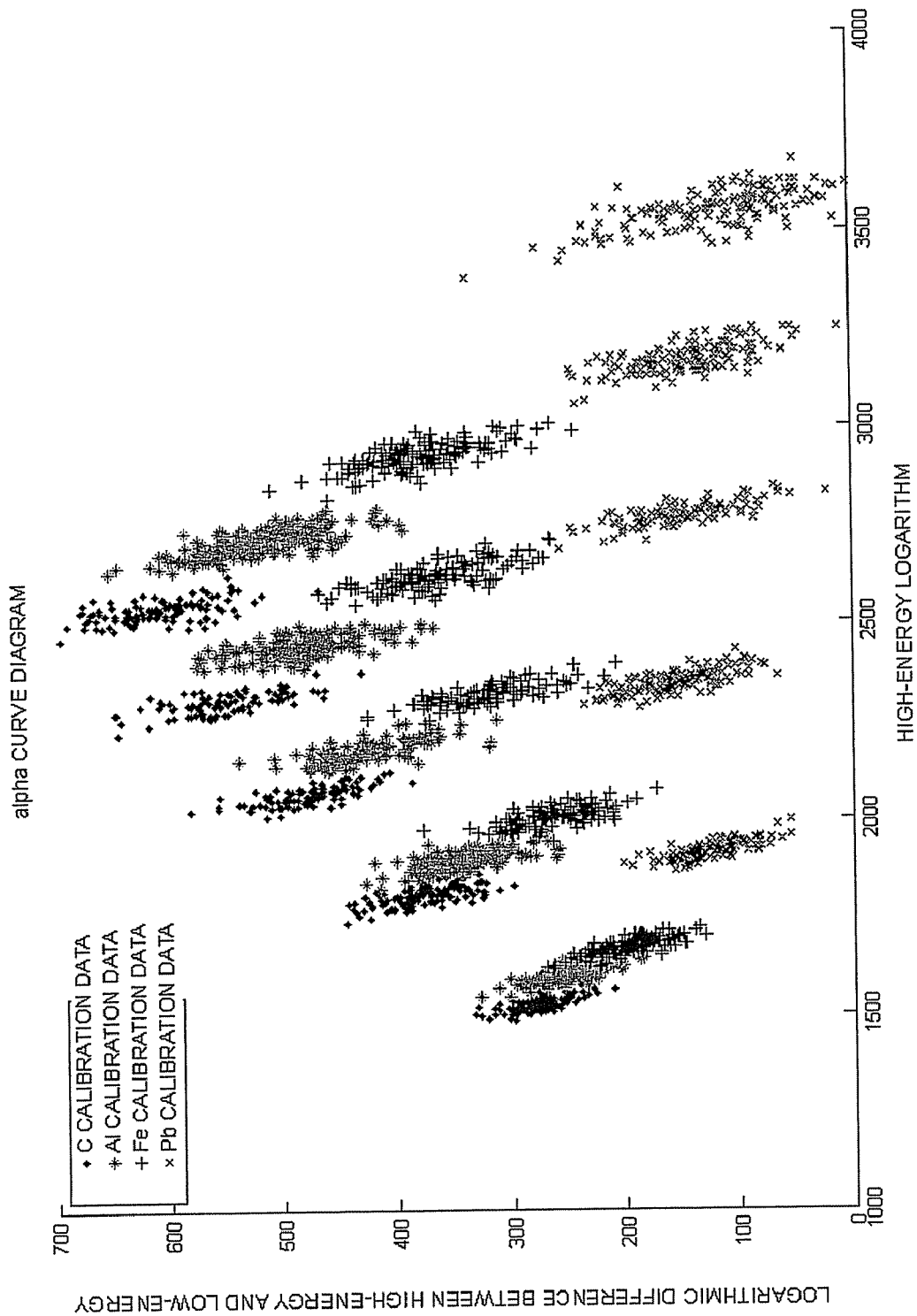
FIG. 6A shows a schematic diagram of training data of calibration materials used during the automatic calibration process.

As described above, at block 130, the data correction module is called to perform a data correction on the original calibration data, to eliminate the effects of background data of the detector, inconsistencies of the detector, and fluctuations of amount of rays, and to obtain training data of the calibration material. FIG. 6A is a schematic diagram of the training data within some detecting span in the alphas curve diagram.

A process for generating a classification boundary among various types of materials from the training data of the calibration material will be described in a greater detail as follows.

(i) Within some detecting span, a mean value statistic is performed sequentially on several columns of corrected dual-energy data of each ladder for each material, so as to obtain a series of mean value points for the training data of the calibration material. FIG. 6C is a schematic diagram of the mean value points for the training data within some detecting span in the alpha curve diagram.

Figure 6B:
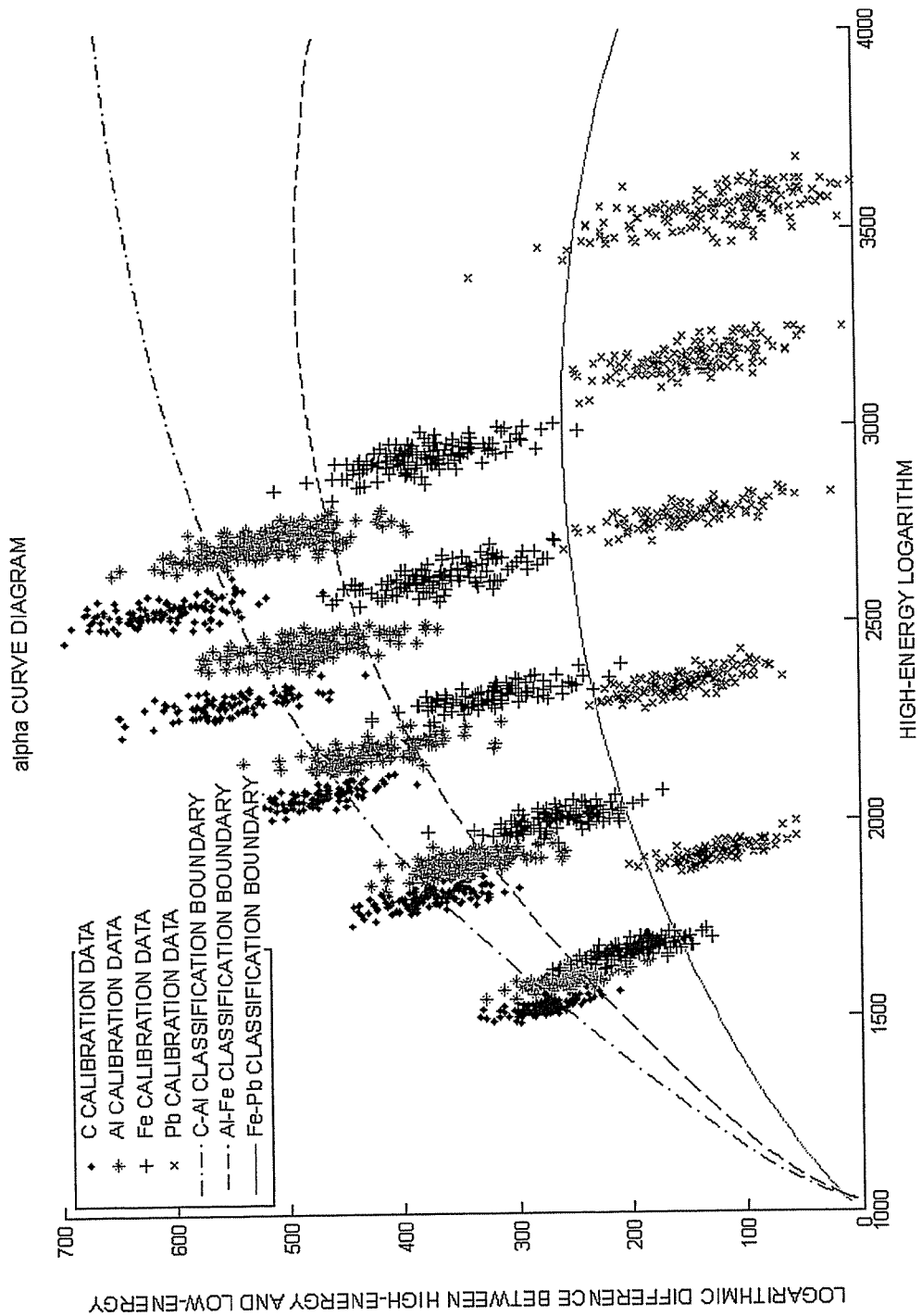
FIG. 6B shows a schematic diagram of an alpha curve generated from the training data of calibration materials.
Figure 6C:
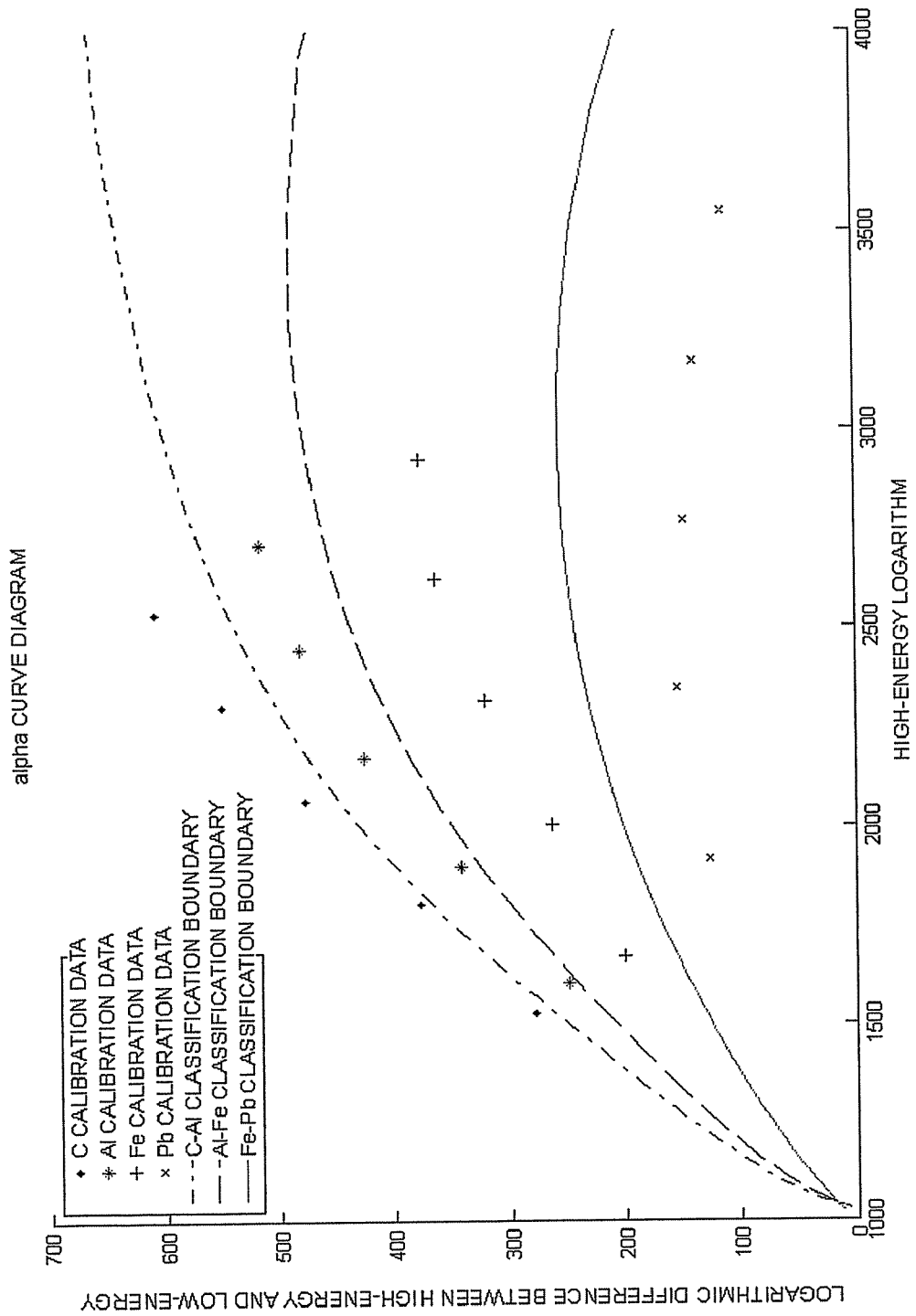
FIG. 6C shows a statistical result of the training data of calibration materials.

(ii) In the alpha curve diagram of FIG. 6B, several mean value points for the training data of some type of material are connected in together, so that a discrete alpha curve for that material may be obtained. However, since the order number of the ladders of the calibration material is limited, the discrete alpha curve obtained directly from connecting is of quite low accuracy. Therefore, the least square curve fitting method can be adopted to perform curve fitting, i.e. to obtain a fitting polynomial of a given data point by means of the least square method. Several mean value points of the training data are considered as input parameters for the curve fitting such that a fitting parameter for the curve, i.e. the coefficients of respective orders of the polynomial, may be obtained. The order of the fitting polynomial is selected relying on the actual situation. The curve fitting may also adopt the other fitting methods, such as the optimum fitting polynomial under Chebyshev.

(iii) A discretization is performed on the x-axis of the alpha curve, the discrete accuracy for which depends on necessities. Then, y-axis data corresponding to each discrete point may be calculated by using the curve fitting parameters. Through this step, a discretization alpha curve for the material may be obtained.

(iv) Repeat steps (ii) and (iii) until the discretization alpha curves for all the materials may be obtained.

(v) As can be seen from FIG. 6B, the alpha curve is of monotonicity in the direction of the atomic number, which is just the foundation for the dual-energy material discrimination algorithm. As a result, discretization alpha curves for various types of materials may be obtained such that a discretization boundary for two adjacent curves may be sequentially calculated, as shown in FIG. 6C.

The classification of the four types of categories depends on the equivalent atomic number: Z=1~10 is classified into a category of organic substance; Z=10~18 is classified into a category of light metals; Z=18~57 is classified into a category of inorganic substance; and Z>57 is classified as a category of heavy metals. Graphite (Z=6), aluminum (Z=13), iron (Z=26) and lead (Z=82) are selected for the four types of typical materials respectively. A discretization alpha curve for an atomic number of Z=10, i.e. a classification boundary between organic substance and inorganic substance, is obtained by performing weighted averaging on a discretization alpha curve for the material of graphite (Z=6) and a discretization alpha curve for the material of aluminum (Z=13). Among the other things, the weighted value of the weighted averaging may be simply calculated based on the atomic number, i.e. it is assumed that distinguishabilities within different ranges of the atomic number are the same. Although distinguishabilities within different ranges of the atomic number should be different by strictly speaking, since the high-energy dual-energy is different from the low-energy dual-energy in that the material discrimination ability thereof is relatively poor, only the materials belonging to different categories may be distinguished, while the materials with different atomic numbers can not be accurately distinguished. Therefore, such difference is acceptable.

Similarly, a discretization alpha curve for an atomic number of Z=18, i.e. a classification boundary between light metals and inorganic substance, is obtained by performing weighted averaging on a discretization alpha curve for the material of aluminum (Z=13) and a discretization alpha curve for the material of lead (Z=82). A discretization alpha curve for an atomic number of Z=57, i.e. a classification boundary between inorganic substance and heavy metals, is obtained by performing weighted averaging on a discretization alpha curve for the material of iron (Z=26) and a discretization alpha curve for the material of lead (Z=82).

(vi) Repeat steps (i), (ii), (iii), (iv) an (v) until discretization classification boundaries for all the detection spans are obtained.

Data for the classification boundaries of various types of typical materials, among various detecting spans, is saved in a file as a classification parameter for the material discrimination module.

As described above, the material discrimination is a distinguished feature for the dual-energy X-ray system from the single-energy X-ray system. Since the material discrimination ability obtained by the high-energy X-ray imaging is much worse than that of the low-energy dual-energy X-ray technology. Therefore, it is required for the material discrimination module to not only consider how to perform a classification correctly, but also consider how to improve the effect of the material discrimination.

First of all, a noise reduction processing is performed on the high-energy transparency and the low-energy transparency. Then a material discrimination processing is performed using a result of the noise reduction. Finally a further noise reduction processing is performed on a result of the material discrimination again. If the requirement of the system for the processing speed is very high, only either of the steps before and after the material discrimination may be left, while still ensuring better effect of the material discrimination.

The material discrimination ability of the high-energy X-ray dual-energy is much worse than that of the low-energy dual-energy X-ray technology, due to the limitation of the energy spectrum where the high-energy X-ray dual-energy exists. However, the statistical fluctuation of the X-ray is inherent. Therefore, it is required to perform a preprocessing on the data, and to perform noise reduction on the high-energy image and the low-energy image, respectively. Otherwise the accuracy of the material discrimination ability will be limited to a great extent. Before performing the noise reduction, the greater the statistical fluctuation is, the lower the classification accuracy is, under the premise of the classification accuracy being lowered to a certain extent. When the classification accuracy is lowered to a certain extent, a classification error is decided. In order to improve the classification accuracy and ensure the effect of the material discrimination, it is necessary to design an efficient preprocessing algorithm to perform noise reduction. The purpose of the preprocessing is to reduce the noise of the data to make the data approach the true value as much as possible, so as to increase the accuracy of the material discrimination. The noise reduction degree of the preprocessing depends on the noise level of the system. The design of the preprocessing algorithm is of a great flexibility as long as the purpose of the noise reduction is achieved. To achieve the effect of the material discrimination as much as possible, it is necessary to focus on the selection of a neighborhood and the definition of a similar point, during the design process for the preprocessing algorithm:

(a) The selection of a neighborhood: the neighborhood should be properly made big, since the number of the statistically averaged points is too small and the effect of the noise reduction is not ideal when the neighborhood is too small. Of course, the neighborhood should not be made too large, since the operating speed will be affected, the effect of the noise reduction will not be further increased, and excessive smooth is possibly caused when the neighborhood is too large.

(b) The definition of a similar point: a fuzzy edge problem will be easily introduced during the statistically averaging process when a large neighborhood is selected. In order to avoid affecting the edge region during the noise reduction, it is required to add a limitation condition for points in the neighborhood during the statistical process. The point agreeing with the condition is referred as a similar point, only by which the mean value statistic is affected. The points belonging to a region different from the center point do not agree with the limitation condition, thereby outside the statistical range, so that they have no effect on the mean value.

Figure 7A:
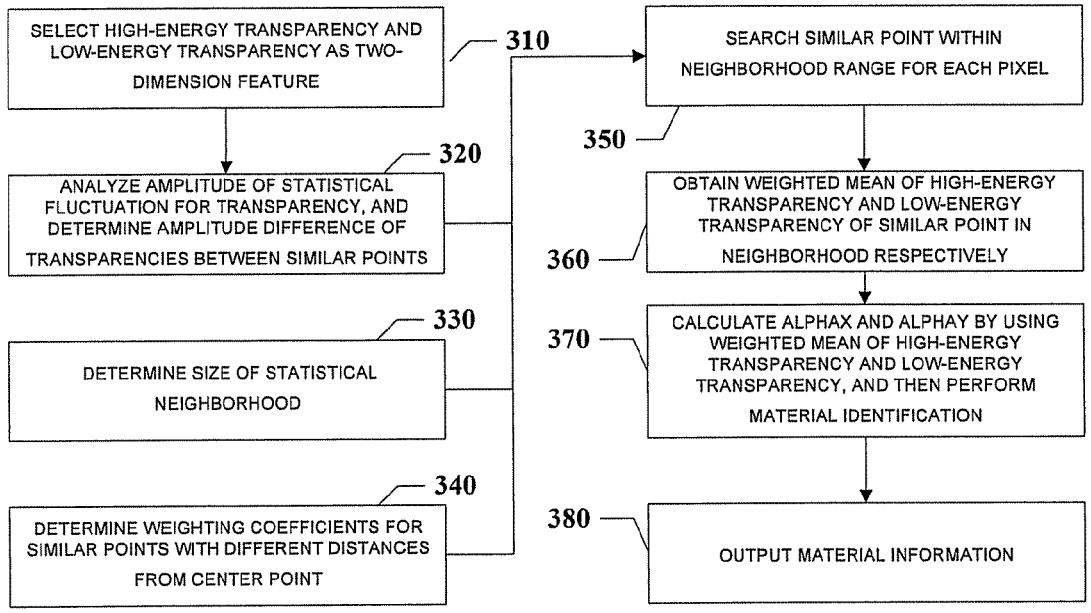
FIG. 7A shows a flowchart of illustrating a dual-energy (i.e. high-energy and low-energy) transparency noise reduction process.

The steps of the preprocessing algorithm are illustrated in the flowchart of FIG. 7A.

In steps 310~340, a parameter of the algorithm is set based on the commonly used features of the dual-energy data during executing of the algorithm. In steps 350~380, a noise reduction operation is performed on actual images based on the parameter of the algorithm determined in steps 310~340 during executing of the algorithm.

In step 310, the high-energy transparency and the low-energy transparency are selected as a two-dimension feature. This is because the dual-energy system may only directly obtain this two-dimension feature. The selection of the two-dimension feature, instead of selecting either of the high-energy transparency or the low-energy transparency, as a one-dimension feature is to ensure the judgment of the similar point is more accurate.

In step 320, it is critical to analyze the amplitude of the statistical fluctuation for the transparency. The amplitude of the statistical fluctuation for the transparency depends on the design level of the overall system. A manner for obtaining the amplitude of the statistical fluctuation is to perform a statistic on a relative standard deviation of the transparency within an even region. In general, the noise is 2.355 times of the standard deviation. It is possible to set an amplitude difference between the transparencies among similar points according to the noise level.

In step 330, the setting of the size of the neighborhood is associated with the amplitude of the data statistical fluctuation in step 320. The area of the neighborhood is set bigger correspondingly, as the amplitude of the statistical fluctuation becomes larger so that the area of the neighborhood should be set bigger. On the other hand, the operating speed of the algorithm becomes slower, as the area of the neighborhood is set bigger. Through the processing for actual data and the comparison of the processing effects of different neighborhoods, an area of 5 pixels*5 pixels is selected for the preprocessing neighborhood in the present system.

In step 340, the setting for the weighting coefficients for the similar points with different distances from the center point is not a critical step for this algorithm. The system adopts a manner of equal weighting summarization to perform.

In step 350, a search range for a similar point is determined for the center pixel, based on the area of the neighborhood determined in step 330. If differences between the high-energy transparency and the low-energy transparency of the center pixel, and those of some pixel in the neighborhood, respectively, are both smaller than the amplitude difference of the transparencies between the similar points determined in step 320, the pixel is considered as a similar point of the center pixel.

In step 360, a weighted averaging is performed on the weighted coefficients determined in step 340 for the high-energy transparency and the low-energy transparency between the similar points, to obtain a weighted mean of the high-energy transparency and the low-energy transparency.

In step 370, alphax and alphay are calculated by using a noise reduction result outputted in step 360, i.e. the weighted mean of the high-energy transparency and the low-energy transparency, for which the calculation formula is referred as FIG. 5.

Finally, a material discrimination is performed, so as to obtain a preliminary result of the material identification.

An alpha curve method is adopted to design a material identification algorithm, characteristic axes thereof are alphax and alphay (a coordinate definition for the alpha curve is illustrated in FIG. 5), respectively. The alphax and alphay are calculated by using the weighted mean of the high-energy transparency and the low-energy transparency. Then a material discrimination is performed. The material discrimination is based on a classification boundary obtained by the automatic calibration module. It can be seen from FIG. 6A that the alpha curve is of monotonicity in the direction of the atomic number, which is also the foundation of the dual-energy material discrimination algorithm. For the high-energy dual-energy, the alphay value monotonously declines in the direction of the atomic number, when the atomic number of the material increases, corresponding to the same alphax point. It is known that alpha data for a point to be inspected is (alphaxR, alphayR), it is possible to obtain three boundary points corresponding to the alphaxR, i.e. alphayC—Al, alphayAl—Fe and alphayFe—Pb respectively, by looking up a table. It is possible to determine material information for the point to be inspected by comparing the relationships among alphayC-Al, alphayAl—Fe and alphayFe—Pb.

The material identification is based on the weighted mean of the similar points. Therefore, the effect of the data statistical fluctuation on the classification accuracy has been reduced to a minimum. However, a material discrimination result between points is not smooth, since the material discrimination is performed one point by one point. To ensure the display effect, a noise reduction is further performed on the material discrimination results of the similar points, after performing material discrimination on a whole image.

Figure 7B:
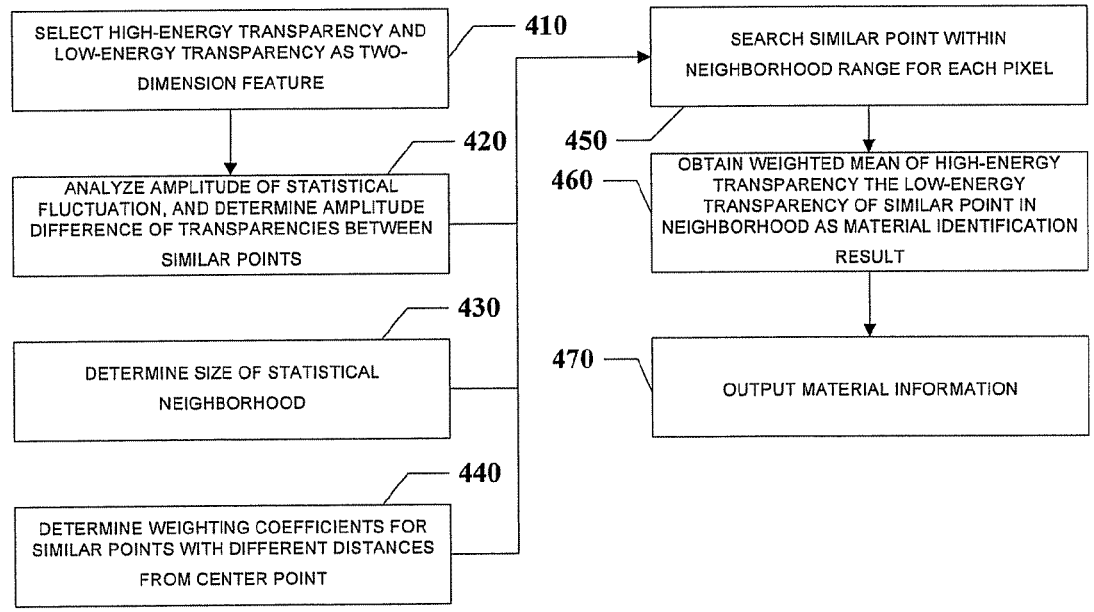
FIG. 7B shows a flowchart of illustrating a noise reduction process performed on a result of material identification.

The noise reduction algorithm is similar with the preprocessing algorithm, the key for which is to select a size for a neighborhood and to judge a similar point. The steps of the algorithm are illustrated in the flowchart of FIG. 7B.

In steps 410~440, a parameter of the algorithm is set based on the commonly used features of the dual-energy data, during the executive process of the algorithm. In steps 450~470, a noise reduction operation is performed on actual images based on the parameter of the algorithm determined in steps 410~440, during the executive process of the algorithm.

In step 410, the high-energy transparency and the low-energy transparency are still selected as a two-dimension feature. Although the preprocessing algorithm and the material identification algorithm are performed, a feature of the material preliminary identification result has been added. However, the added one-dimension feature is obtained based on the previous two-dimension feature without increasing amount of information. Instead, since the noise in the material preliminary identification result is large, which may affect the judgment for the similar point, this one-dimension feature is not selected.

In step 420, it is critical to analyze the amplitude of the statistical fluctuation for the transparency. The amplitude of the statistical fluctuation for the transparency depends on the design level of the overall system. A manner for obtaining the amplitude of the statistical fluctuation is to perform a statistic on a relative standard deviation of the transparency within an even region. In general, the noise is 2.355 times of the standard deviation. It is possible to set an amplitude difference of transparencies between similar points according to the noise level.

In step 430, the setting of the size of the neighborhood is associated with the amplitude of the data statistical fluctuation in step 420. The area of the neighborhood is set bigger correspondingly, as the amplitude of the statistical fluctuation becomes greater, so that the area of the neighborhood should be set bigger. On the other hand, the operating speed of the algorithm becomes slower, as the area of the neighborhood is set bigger. To ensure the color visual effect, the strength for the noise reduction is properly enhanced, and an area of 11 pixels*11 pixels is selected for the neighborhood.

In step 440, the setting of the weighting coefficients for the similar points with different distances from the center point is not a critical step for this algorithm. The system adopts a manner of equal weighting summarization to perform.

In step 450, a search scope for the similar point is determined for the center pixel, based on the area of the neighborhood determined in step 430. If differences between the high-energy transparency and the low-energy transparency of the center pixel, and those of some pixel in the neighborhood, respectively, are both smaller than the amplitude difference of the transparencies between the similar points determined in step 420, the pixel is considered as a similar point of the center pixel.

In step 460, a weighted averaging is performed on the weighted coefficients determined in step 440 for the high-energy transparency and the low-energy transparency between the similar points, to obtain a weighted mean of the high-energy transparency and the low-energy transparency.

In step 470, the weighted mean of the material identification result obtained in step 460 is outputted as a final material identification result.

Figure 8:
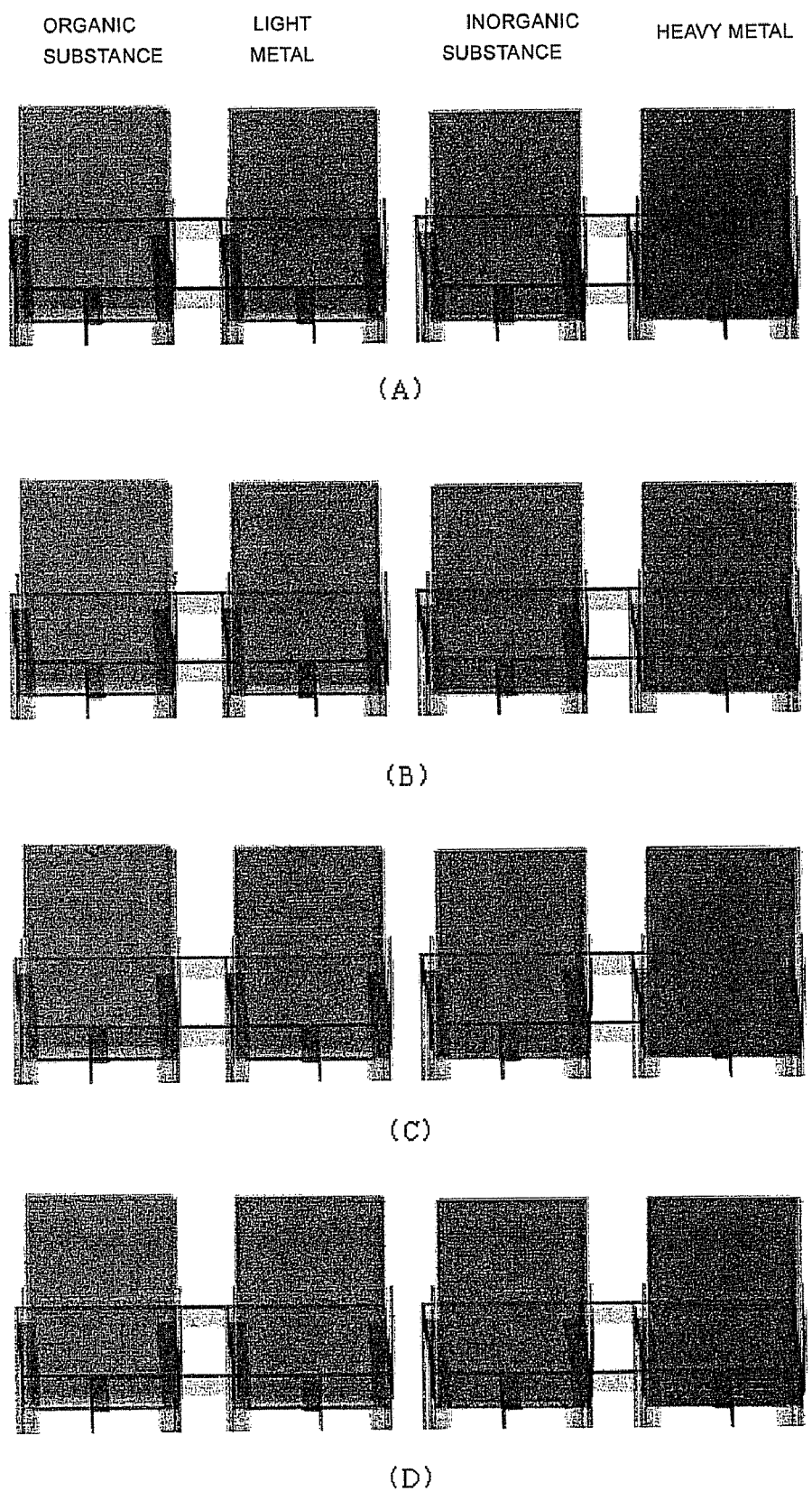
FIG. 8 shows imaging results generated for different pre-processing parameters by a material discrimination module.

FIG. 8 gives a contrast of effect diagrams for different processing parameters in the material discrimination module. As shown in (A) of FIG. 8, the noise in the material identification result is very large and the material discrimination accuracy is affected significantly, when no preprocessing is performed. As shown in (B) of FIG. 8, when a smaller neighborhood (3*3) is selected to perform preprocessing, the noise is reduced somewhat, but the noise reduction extent is very limited. As shown in (C) of FIG. 8, when a larger neighborhood (11*11) is selected to perform preprocessing without performing similar point judgment, the noise in the image is reduced significantly, however, in the edge region of the object, the material discrimination result is obviously wrong, since the data of two types of materials are mixed together for statistic. As shown in (D) of FIG. 8, when a larger neighborhood of 11*11 is selected to perform preprocessing and similar point judgment, it is possible to function as a noise reduction without affecting the edge region.

The basic idea of the gray-scale fusion module lies in that, the low-energy level imaging image predominate in the region penetrating a low-mass thickness, and that the high-energy level imaging image predominate in the region penetrating a high-mass thickness. The specific weighting factors may be flexibly adjusted depending on the features of the actual system. Based on this idea, the following formula may be adopted as follows: resultGray=nIl*dFactor+nIh*(1−dFactor) wherein, nil, nIh and resultGray are low-energy level data, high-energy level data and fusion gray-scale, respectively, and dFactor is a weighting factor, which may be nIl/max (nIl) or nIh/max (nIh).

In the colorization module, the key points are a design for the corresponding relationship between the material information and the hue and a design for the color table.

There have been international standards for color display in the low-energy X-ray dual-energy system, with organic substance in orange, light metals in green, and inorganic substance in blue. A color standard for the high-energy X-ray dual-energy system has not been developed. Taking the user's visual habits into account, it is possible to continue to use the color display standard of the low-energy X-ray dual-energy system, still indicating organic substance in orange, light metals in green, and inorganic substance in blue. In addition to the above three categories, i.e. organic substance, light metals and inorganic substance, the high-energy X-ray dual-energy system may further distinguish the category of heavy metals, display for which has no available standard and may be set based on the designer's preference. Taking the continuity of the use of the hue into account, the system may indicate heavy metals in purple.

Figure 9:
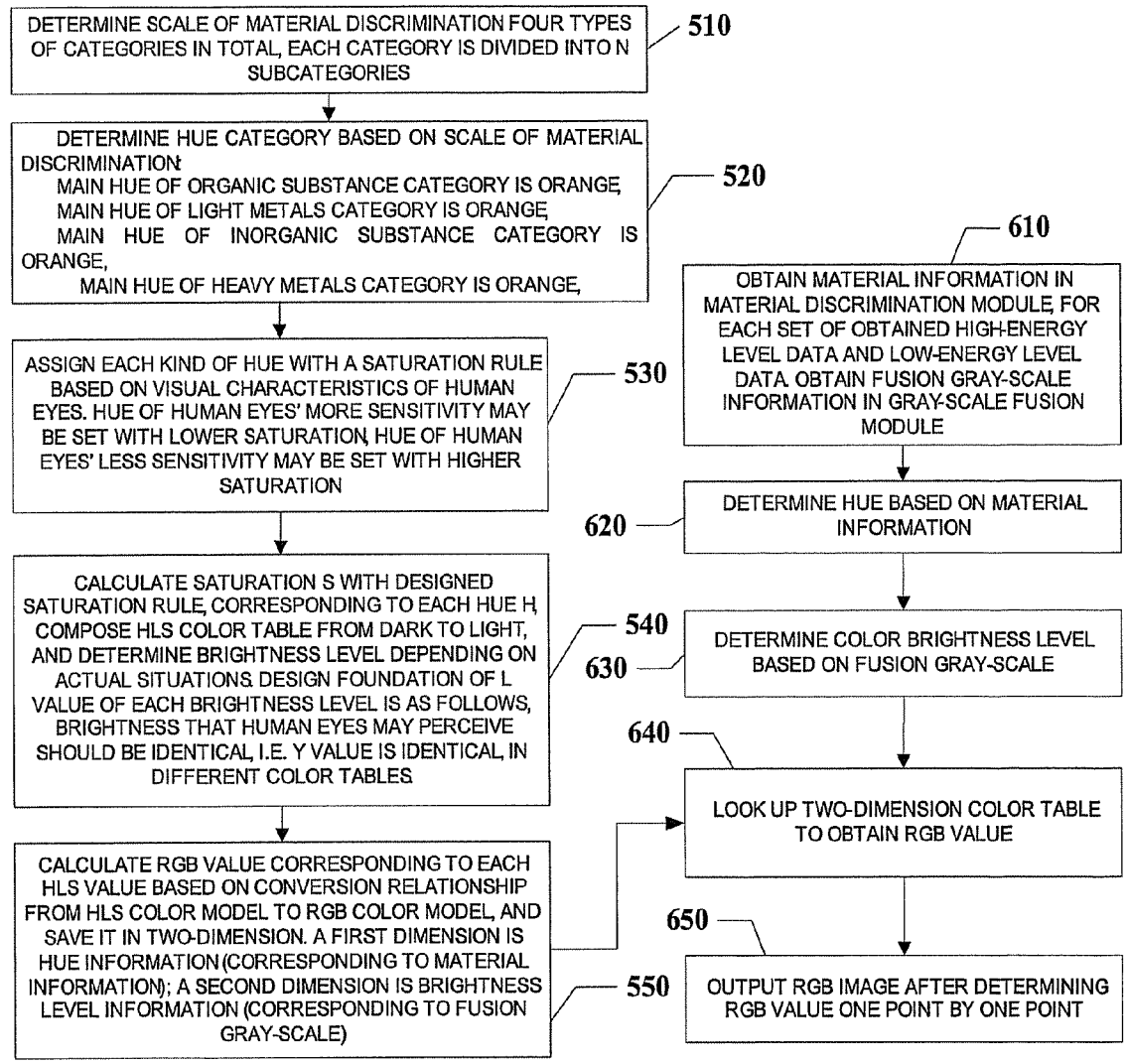
FIG. 9 shows a schematic diagram for illustrating a generation process of a color table and a generation process of a RGB image.

The key points of the colorization algorithm lie in a design of the color table as well as mapping relationships among the atomic number and the fusion gray-scale, and the color information. The colorization flow is illustrated in FIG. 9. In steps 510~550, a design principle for the color table is explained. In steps 610~650, a mapping principle among the atomic number and the fusion gray-scale, and the color information is explained.

In steps 510 and 520, the atomic number is correlated with a hue H (H in HLS color model), wherein different atomic numbers are indicated with different hues, and the number of the categories for the material discrimination is identical with that of the hues. For the coordination of color images, it is possible to refine the categories during the material discrimination process, i.e. not only dividing substance into four categories, i.e. organic substance, light metals, inorganic substance, and heavy metals, but also further refining substance into several subcategories based on the atomic number within each category. The design of the hues make a compromise between the major principles of following the color display standard and the hue transitions from orange to orange yellow, from yellow green to bluish green, from cyanine to navy blue, and from violet-blue to purplish read.

In step 530, an appropriate saturation value is set for each hue, according to the visual theory. Human eyes are of more sensitivity on green hue, of general sensitivity on orange hue, and of less sensitivity on blue hue. Therefore, green hue may be assigned with a lower saturation degree, orange hue may be assigned with a saturation degree more than middle, and blue hue may be assigned with a higher saturation degree. Based on this principle, a corresponding rule between the saturation degree and the hue is designed.

In step 540, it is critical to design a mapping relationship between the fusion gray-scale and L value (L value in HLS color model). In order to ensure the coordination of hues, in a color table with different hues, a brightness the human eyes may perceive should be equivalent for colors with the same brightness level, while the fusion gray-scale should not be simply considered as identical with the L value.

This step needs to rely on a Y value in YUV color model. The y value in YUV color model represents a brightness that human eyes may perceive, and the L value in HLS color model can not represent a brightness that human eyes may perceive. If the color table is designed simply based on the corresponding between the fusion gray-scale and the L value, the colors of different hues are not coordinated. Therefore, it is necessary to design a mapping relationship between the fusion gray-scale and the L value by integrating conversion relationships among YUV model, RGB model and HLS model based on a principle, in which the fusion gray-scale is identical with the Y value, so as to obtain a HLS color table.

Since a brightness human eyes may perceive may be indicated by a Y value in YUV color model, the Y values of the same brightness level should be identical. As a result, the problem may be converted into a very simple mathematical problem, where it is required to determine a brightness L value in HLS color model, when a hue H in HLS color model and its saturation degree S and a Y value in YUV model are already known. Since there is no direct conversion relationship between YUV color model and HLS color model, it may be performed by taking RGB model as an intermediary.

In step 540, a conversion from HLS color table to RGB color table may be completed. Since the conversion from HLS color model to RGB color model is time consuming, a relationship between the both should be calculated in advance and saved in a table, so that it is possible to obtain a RGB value by directly looking up the table. A two-dimension mapping table from HLS to RGB is composed, in which RGB values are stored. A first dimension of the two-dimension is a material information index, a second dimension thereof is a fusion gray-scale index. As a result, a RGB value of each point may be obtained by looking up the table after obtaining substance-identified material information and a fused gray-scale, for color image display.

After the design of the color table, a real-time color process is a simple table look-up process, in which the two-dimension RGB color table is looked up by using the material information outputted from the material discrimination module and the fusion gray-scale information outputted from the gray-scale fusion module, so as to obtain a color image.

In step 610, the material information outputted from the material discrimination module and the fusion gray-scale information outputted from the gray-scale fusion module are obtained as input information for the colorization algorithm.

In step 620, a value of the first dimension index of the RGB two-dimension mapping tale is determined based on the material information (corresponding to the hues).

In step 630, a value of the second dimension index of the RGB two-dimension mapping tale is determined based on the fusion gray-scale information (color brightness level).

In step 640, a RGB value is obtained by looking up the two-dimension RGB color table, based on the two indexes determined in steps 620 and 630 respectively.

In step 650, steps 610~640 are repeated, RGB values are determined one point by one point, and then a color image is outputted.

Effects of the gray-scale display and the color display after the material discrimination are illustrated in FIG. 10.

The present invention has been described hereinabove in combination with the preferred embodiments. It should be appreciated for those skilled in the field that any other variations, substitutions and additives will be made without departing from the spirit and scope of the invention. Therefore, the scope of the present invention is not intended to be limited to the above specific embodiments, and should be defined by the appended claims.

What is claimed is:

1. A method for substance identification comprising steps of:
    transmitting an object under inspection using high-energy rays and low-energy rays to obtain a high-energy transmission image and a low-energy transmission image for the object, wherein a value of each pixel in the high-energy image indicates a high-energy transparency of the high-energy rays with respect to corresponding parts of the object, and a value of each pixel in the low-energy image indicates a low-energy transparency of the low-energy rays with respect to corresponding parts of the object;
    calculating a value of a first function for the high-energy transparency and a value of a second function for the high-energy transparency and the low-energy transparency, for each pixel; and
    classifying locations determined by the value of the first function and the value of the second function using a pre-created classification curve, so as to identify the type of the substance of a part of the object corresponding to each pixel,
    wherein the classification curve is created for each type of calibration material through the following steps:
    obtaining corresponding high-energy transparency and low-energy transparency by irradiating calibration materials with various thicknesses using the high-energy rays and the low-energy rays;
    forming points of the calibration materials with difference thicknesses by taking the first function of the high-energy transparency as an abscissa and the second function of the low-energy transparency and the high-energy transparency as an ordinate; and
    forming the classification curve based on the points.

2. The method of claim 1, further comprising steps of:
    setting a neighborhood with a preset size; and
    performing noise reduction on the high-energy image and the low-energy transmission image in the neighborhood of each pixel.

3. The method of claim 2, wherein the step of performing noise reduction on the high-energy image and the low-energy transmission image in the neighborhood of each pixel comprises steps of:
    searching a pixel similar with the center pixel in the neighborhood as a similar pixel; and
    performing weighted averaging on the similar pixel in the neighborhood.

4. The method of claim 3, wherein differences between the high-energy transparency and the low-energy transparency of the similar pixel, and the high-energy transparency and the low-energy transparency of the center pixel, respectively, are both lower than a preset value.

5. The method of claim 3, wherein the object is identified as organic substance, light metals, inorganic substance or heavy metals.

6. The method of claim 5, further comprising a step of performing colorization display on an identification result.

7. The method of claim 6, wherein the step of performing colorization display comprises:
    performing weighted averaging on the high-energy transparency and the low-energy transparency of each pixel as a fusion gray-scale value;
    determining a hue according to the type of the material of a part of the object corresponding to the pixel;
    determining a brightness level of the pixel according to the fusion gray-scale value of the pixel; and
    obtaining a R value, G value and B value of the pixel from a pre-created look-up table by taking the hue and the brightness level as indices.

8. The method of claim 7, wherein, the step of determining a hue according to the type of the material of a part of the object corresponding to the pixel comprises steps of: assigning orange to organic substance, assigning green to light metals, assigning blue to inorganic substance, and assigning purple to heavy metals.

9. The method of claim 1, further comprising a step of performing spectrum shaping on rays emitted from a ray source so as to enlarge an energy spectrum difference between the high-energy rays and the low-energy rays.

10. The method of claim 1, wherein the step of forming the classification curve based on the points comprises adopting a least square curve fitting method to perform curve fitting on the points.

11. The method of claim 1, wherein the step of forming said classification curve based on the points comprises:
    adopting the optimum fitting polynomial under Chebyshev to perform curve fitting on the points.

12. The method of claim 1, further comprising a step of performing discretization on the classification curve.

13. An apparatus for substance identification comprising:
    image forming means for transmitting an object under inspection using high-energy rays and low-energy rays to obtain a high-energy transmission image and a low-energy transmission image for the object, wherein a value of each pixel in the high-energy image indicates a high-energy transparency of the high-energy rays with respect to corresponding parts of the object, and a value of each pixel in the low-energy image indicates a low-energy transparency of the low-energy rays with respect to corresponding parts of the object;
    calculating means for calculating a value of a first function for the high-energy transparency and a value of a second function for the high-energy transparency and the low-energy transparency, for each pixel; and
    classifying means for classifying locations determined by the value of the first function and the value of the second function using a pre-created classification curve, so as to identify the type of the substance of a part of the object corresponding to each pixel;

wherein the classification curve is created for each type of calibration material by:
  obtaining corresponding high-energy transparency and low-energy transparency by irradiating calibration materials with various thicknesses using the high-energy rays and the low-energy rays;
  forming points of the calibration materials with difference thicknesses by taking the first function of the high-energy transparency as an abscissa and the second function of the low-energy transparency and the high-energy transparency as an ordinate; and
  forming the classification curve based on the points.

14. The apparatus as claim 13, further comprising:
means for setting a neighborhood with a preset size; and
means for performing noise reduction on the high-energy image and the low-energy transmission image in a neighborhood of each pixel.

15. The apparatus of claim 14, wherein the means for performing noise reduction on the high-energy image and the low-energy transmission image in the neighborhood of each pixel comprises:
  means for searching a pixel similar with the center pixel in the neighborhood as a similar pixel; and
  means for performing weighted averaging on the similar pixel in the neighborhood.

16. The apparatus of claim 15, wherein differences between the high-energy transparency and the low-energy transparency of the similar pixel, and the high-energy transparency and the low-energy transparency of the center pixel, respectively, are both lower than a preset value.

17. The apparatus of claim 15, wherein the object is identified as organic substance, light metals, inorganic substance or heavy metals.

18. The apparatus of claim 17, further comprising means of performing colorization display on an identification result.

19. The apparatus of claim 18, wherein the means of performing colorization display comprises:
  means for performing weighted averaging on the high-energy transparency and the low-energy transparency of each pixel as a fusion gray-scale value;
  means for determining a hue according to the type of the material of a part of the object corresponding to the pixel;
  means for determining a brightness level of the pixel according to the fusion gray-scale value of the pixel; and
  means for obtaining a R value, G value and B value of the pixel from a pre-created look-up table by taking the hue and the brightness level as indices.

20. The apparatus of claim 19, wherein organic substance is assigned with orange, light metals are assigned with green, inorganic substance is assigned with blue, heavy metals are assigned with purple.

21. The apparatus of claim 13, further comprising means of performing spectrum shaping on rays emitted from a ray source, so as to enlarge an energy spectrum difference between the high-energy rays and the low-energy rays.

22. The apparatus of claim 13, wherein a least square curve fitting method is adopted to perform curve fitting on the points.

23. The apparatus of claim 13, wherein an optimum fitting polynomial under Chebyshev is adopted to perform curve fitting on the points.

24. The apparatus of claim 13, wherein a discretization is performed on the classification curve.

* * * * *